US00PP12080P2

(12) United States Plant Patent
Plevier

(10) Patent No.: US PP12,080 P2
(45) Date of Patent: Sep. 11, 2001

(54) ALSTROEMERIA PLANT NAMED 'PERFECT LOVE'

(75) Inventor: F. B. Plevier, Sassenheim (NL)

(73) Assignee: Koninklijke van Zanten B.V., Hillegom (NL)

( * ) Notice: Subject to any disclaimer, the term of this patent is extended or adjusted under 35 U.S.C. 154(b) by 0 days.

(21) Appl. No.: 09/174,836

(22) Filed: Oct. 19, 1998

(51) Int. Cl.[7] ..... A01H 5/00
(52) U.S. Cl. ..... Plt./309
(58) Field of Search ..... Plt./309

(56) References Cited

PUBLICATIONS

UPOV–ROM, 1999/02, Plant Variety Database, GTI Jouve Retrieval Software, 2 citations for 'Perfect Love'.*

* cited by examiner

*Primary Examiner*—Howard J. Locker
(74) *Attorney, Agent, or Firm*—Christie, Parker & Hale, LLP

(57) ABSTRACT

A new and distinct Alstroemeria plant variety producing light purple flowers with yellow coloration of center.

1 Drawing Sheet

BACKGROUND OF THE INVENTION

The present invention relates to a new and distinct variety of Alstroemeria which is a cross of two unnamed, undistributed seedlings. The varietal denomination of the new variety is 'Perfect Love'.

The first act of asexual reproduction of 'Perfect Love' was in Rijsenhout, The Netherlands, by micropropagation (tissue culture). Asexual reproduction by tissue culture through successive generations in Rijsenhout, The Netherlands, has demonstrated that the combination of characteristics as herein disclosed for 'Perfect Love' are firmly fixed and retained through successive generations.

SUMMARY OF THE INVENTION

The new variety of Alstroemeria, 'Perfect Love', produces light purple flowers with yellow coloration towards center and almost lacking stripes.

DESCRIPTION OF THE ILLUSTRATION

The new variety of Alstroemeria hybrid is illustrated in the accompanying illustration, which shows typical flower and stem characteristics, with colors being as nearly true as is possible for illustrations of this type.

DETAILED DESCRIPTION OF THE NEW VARIETY

The following is a detailed description of the new cultivar of Alstroemeria as observed in a greenhouse in Rijsenhout, The Netherlands in the month of April. Color designations indicated are in accordance with The Royal Horticultural Society Color Chart by color plate designations.

'Perfect Love' has not been observed under all possible environmental conditions. Phenotypic expression may vary with variations in environment such as temperature, light intensity and day length, and growing and cultural conditions.

Classification:
*Family.*—Alstroemeriaceae.

*Botanic and commercial.*—Alstroemeria hybrid.

Plant:
*Form.*—Bush.
*Shape.*—Upright.
*Height.*—25 to 40 cm.
*Growth rate.*—Medium and vigorous. Length of time from rooted plants to flowering stage under commercial greenhouse conditions is 75–90 days.
*Pinching.*—None required.
*Main stem length.*—About 30 cm.
*Internode length.*—About 0.5 to 3 cm.
*Strength.*—Strong and erect.
*Foliage.*—Quantity: Abundant. Number of leaves: About 10–20 per stem. Size of leaf: Length about 1–10 cm; width about 0.5–3 cm. Shape of leaf: Elliptical. Margin type: Minutely crimped.
*Coloration.*—Upper side: Near 137A. Under side: Near 137B.

Rhizomes:
*Color.*—Near 155A.
*Size.*—About 5–25 cm in length.

Blooming habit: Continuous; pinching not required to maintain plant in continuous blooming condition; blooms have no fragrance.

Blooms: Profusely in spring and fall.
*Size.*—Small; diameter of about 5 cm; depth of about 4 cm.
*Borne.*—In umbels of 3–7 blooms.
*Lastingness.*—On plant: About 3 weeks. Cut flower: About 10–14 days.
*Shape or form.*—When bloom first opens: Cup. When bloom matures: Cup.

Tepelage:
*Number of tepals.*—6.
*Arrangement.*—Two concentric circles of three tepals.
*Form.*—Inner tepals long obovate; outer tepals somewhat cordate and oblong.
*Margin.*—Slightly undulated.
*Apex.*—Pointed.
*Duration of tepals.*—About 3 weeks on stem, tepals drop cleanly.

*Texture.*—Soft.

*Appearance.*—Velvety.

*Coloration of outer tepals.*—Body: Near 77B with purplish green area at the tip on both upper and lower surfaces. Base: Near 77B.

*Coloration of inner lateral tepals.*—Body: Near 9A in midsection changing to near white 155D and then to near Purple Group 77B on outer half on both upper and lower surfaces. Upper surface has 0–5 spots, color near 187A. Base: Near 4D.

*Coloration of inner median tepal.*—Body: Near 77B on both upper and lower surfaces, no spots. Base: Near 4D.

*General.*—Only slight discoloration after full bloom, color become slightly more intensive as bloom ages.

Pedicel:

*Length.*—About 1 to 5 cm.

*Color.*—Near 178B.

*Strength.*—Strong.

*Aspect.*—Upright.

*Character.*—Erect, somewhat hairy.

Bud:

*Diameter.*—About 1–2 cm.

*Length.*—About 0.5–5 cm.

*Shape.*—Pear-shaped to ovoid.

*Opening.*—Buds open from the lower most to the top.

*Color of tepals.*—When tepals first divide: Near 77B. When tepals begin to unfurl: Near 54A.

Reproductive organs:

*Stamen.*—Arranged side by side around the style. Anthers: About 6–8 mm in length; color near 191A. Filaments: About 3.5–4 cm in length; color near 73A. Pollen: Present; color near 160A.

*Pistils.*—One. Styles: About 4–5 cm in length; color near 60D. Stigma: Color near 60D. Fruit: Fertile; ovoid; color at maturity near 163A; about 3–5 cm in length.

I claim:

1. A new Alstroemeria plant of the variety substantially as herein shown and described.

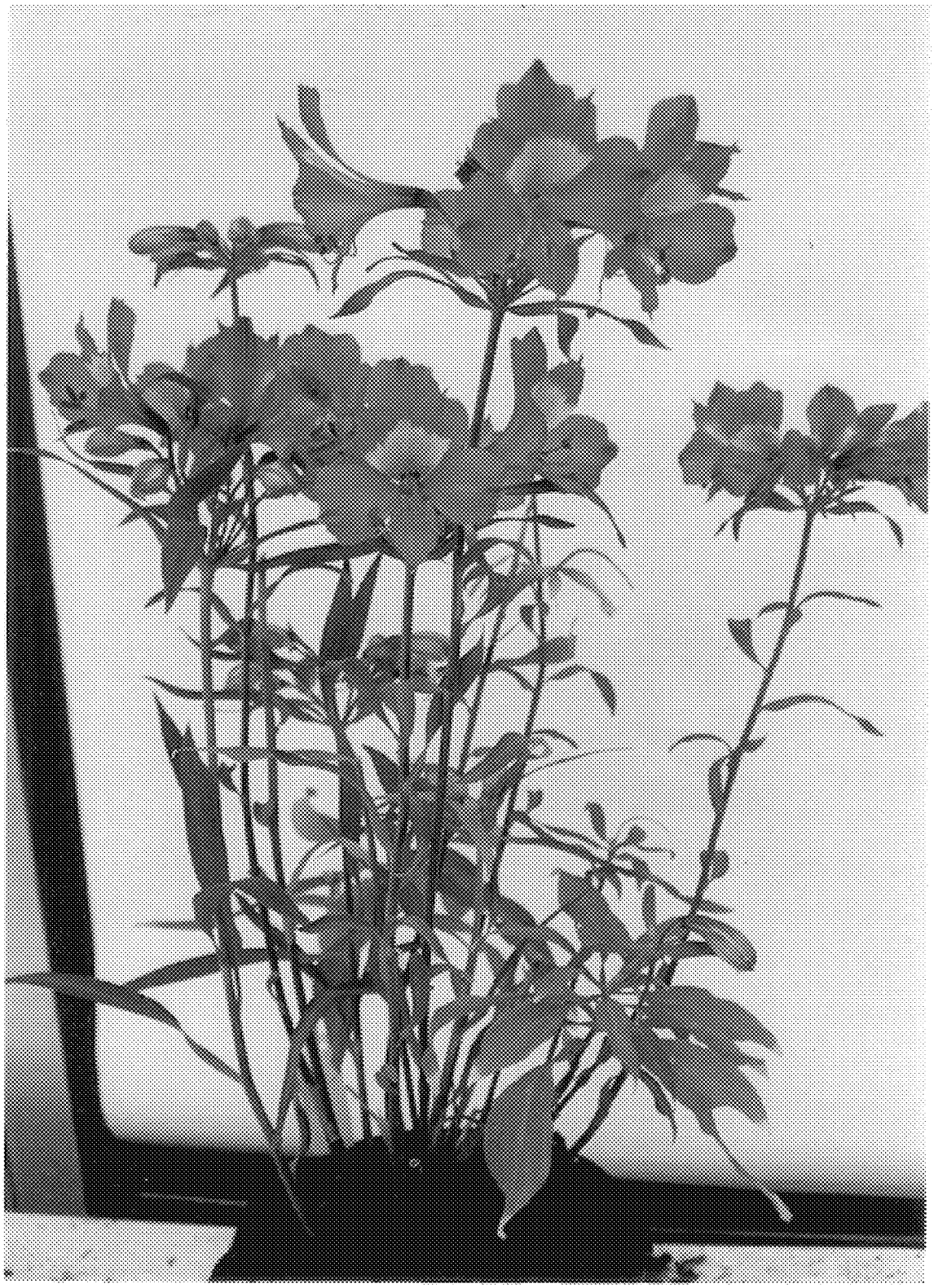

* * * * *